(12) United States Patent
Ciullo

(10) Patent No.: US 12,109,181 B2
(45) Date of Patent: Oct. 8, 2024

(54) LIDOCAINE PATCH AND METHODS OF USE THEREOF

(71) Applicant: James Ciullo, Elmhurst, IL (US)

(72) Inventor: James Ciullo, Elmhurst, IL (US)

(*) Notice: Subject to any disclaimer, the term of this patent is extended or adjusted under 35 U.S.C. 154(b) by 351 days.

(21) Appl. No.: 16/785,269

(22) Filed: Feb. 7, 2020

(65) Prior Publication Data
US 2020/0179314 A1    Jun. 11, 2020

Related U.S. Application Data

(62) Division of application No. 13/722,458, filed on Dec. 20, 2012.

(51) Int. Cl.
| | | |
|---|---|---|
| A61K 31/167 | (2006.01) |
| A61K 9/00 | (2006.01) |
| A61K 9/70 | (2006.01) |
| A61N 1/04 | (2006.01) |
| A61N 1/30 | (2006.01) |

(52) U.S. Cl.
CPC .......... *A61K 31/167* (2013.01); *A61K 9/0009* (2013.01); *A61K 9/7023* (2013.01); *A61N 1/0448* (2013.01); *A61N 1/30* (2013.01)

(58) Field of Classification Search
CPC .. A61K 31/167; A61K 9/0009; A61K 9/7023; A61N 1/0448; A61N 1/30
See application file for complete search history.

(56) References Cited

U.S. PATENT DOCUMENTS

2006/0018976 A1* 1/2006 Bentley .................. A61K 45/06
424/724

FOREIGN PATENT DOCUMENTS

| JP | (1996)0132169 | 12/1997 | |
|---|---|---|---|
| JP | P2000-114834 | 10/2001 | |
| WO | WO-2004037861 A2 * | 5/2004 | ............. C07K 16/22 |

OTHER PUBLICATIONS

Pande (Abstract) (Year: 2010).*
Chinhin ( Machine Translation). (Year: 1997).*
Wang (SciFinder Scholar Abstract Translation) (Year: 2008).*
Kim et al (Year: 2003).*
Chinhin (Year: 1997).*
Wang (Year: 2008).*
CN102018696A, Machine Translation (Year: 2011).*
JH09315964A, Machine Translation (Year: 1997).*
Pande (Year: 2010).*
Gammaitoni (Year: 2004).*
JP2001302501A, Machine Translation (Year: 2001).*
Sesay (Year: 2002).*
Canalis (Year: 2007).*
Holroyd (Year: 2008).*
CN102018696A, Machine Translation (Year: 2001).*
Chapurlat et.al, Deterioration of Cortical and Trabecular Microstructure Identifies Women With Osteopenia or Normal Bone Mineral Density at.
Journal of Bone and Mineral Research, May 2020, p. 833-844, vol. 35 issue 5.
Sharma et. al, Deterioration of Cortical Bone Microarchitecture: Critical Component of Renal Osteodystrophy Evaluation.
American Journal of Nephrology, 2018, 47 pp. 376-384.
Dequeker et al., Bone density and osteoarthritis, The Journal of rheumatology. Supplement, Feb. 1, 1995, 98-100:43.
Lavally, et al. Development of a clinical prediction algorithm for knee osteoarthritis structural progression in a cohort study: value of adding.
Lo, et al., Knee Alignment Is Quantitatively Related to Periarticular Bone Morphometry and Density, Especially in Patients With Osteoarthritis.
Hirvasniei, et al. Bone Density and Texture from Minimally Post-Processed Knee Radiographs in Subjects with Knee Osteoarthritis. Ann.
Stewart et al, Bone density and bone turnover in patients with osteoarthritis and osteoporosis, The Journal of Rheumatology, Mar. 1.
Stewart et al., Bone mineral density in osteoarthritis, Rheumatology: Sep. 2000—vol. 12—Issue 5—p. 464-467.
Geusens et al., Osteoporosis and osteoarthritis shared mechanisms and epidemiology, Current Opinion in Rheumatology: Mar. 2016—vol. 28.
Belmonte-Serrano et al., The relationship between spinal and peripheral osteoarthritis and bone density measurements, The Journal of.
Delgado-Calle et al., Arthritis & Rheumatism, vol. 65, No. 1, Jan. 2013, pp. 197-205.
Marcelli et al.. The relationship between osteoarthritis of the hands, bone mineral density, and osteoporotic fractures in elderly women.
Pramanick et al. "Excipient selection in parenteral formulation development." Pharma Times 45, No. 3 (2013): 65-77.
Choi, Catherine Y. "Chronic pain and opiate management." Dis Mon 62, No. 9 (2016): 334-45.
Busardo et al, Forensic Science International, vol. 256, 2015, pp. 17-20.
Dryden et. al, The Use of Intravenous Lidocaine as an Analgesic Modality in the Austere Environment: Two Cases, Wilderness &.
Kanai et. al, Anesthesia and Analgesia. Mar. 1998;86(3):569-573.

(Continued)

*Primary Examiner* — Jeffrey S Lundgren
*Assistant Examiner* — Ibrahim D Bori
(74) *Attorney, Agent, or Firm* — Lawrence Pope

(57) ABSTRACT

This invention is directed to a transdermal delivery patch comprising local anesthetic agent and optionally a permeation enhancement agent for reducing neuropathic pain.

6 Claims, 2 Drawing Sheets

(56) References Cited

OTHER PUBLICATIONS

Hodgson PS, Neal JM, Pollock JE, Liu SS. The neurotoxicity of drugs given intrathecally (spinal). Anesth Analg. Apr. 1999;88(4):797-809.
Johnson, Regional Anesthesia: 1997; vol. 22 No. 2S March-April Supplement.
Xylocaine Package Insert.
Sekimoto K, Tobe M, Saito S. Local anesthetic toxicity: acute and chronic management. Acute Med Surg. Mar. 6, 2017;4(2):152-160.
Pollock, et al; Dilution of Spinal Lidocaine Does Not Alter the Incidence of Transient Neurologic Symptoms . Anesthesiology1999; 90:445-450.
E. Hernlund et al, Osteoporosis in the European Union: medical management, epidemiology and economic burden: A report prepared in collaboration with the International Osteoporosis Foundation (IOF) and the European Federation of Pharmaceutical Industry Associations (EFPIA) Arch Osteoporos (2013) 8:136.
Catalano, A., Martino, G., Morabito, N. et al. Pain in Osteoporosis: From Pathophysiology to Therapeutic Approach. Drugs Aging 34, 755-765.
Hayashi Y. [Bone diseases with Pain. Osteoporosis]. Clinical Calcium. Apr. 2007;17(4):606-612. DOI: clica0704606612. PMID: 17404492.
S. Scharla, et al., (2006) Skeletal pain in postmenopausal women with osteoporosis:., Current Medical Research and Opinion, 22:12, 2393-2402.
P. Peris, et al., Aetiology and Presenting Symptoms in Male Osteoporosis, Rheumatology, vol. 34,(10), Oct. 1995, 936-941.
Nagel (2006) A Review of: "Pharmaceutical Calculations, 4th Edition", Drug Development and Industrial Pharmacy, 32:1, 139.
Brown, Michael C., American Journal of Pharmaceutical Education; Alexandria vol. 67, Iss. 1/4, (2003): 273-280.
Sharma. Pharmacy Calculations. [Updated Jun. 23, 2022]. In: StatPearls [Internet]. Treasure Island (FL): StatPearls Publishing; 2022.
Gammaitoni, et al., (2003), Safety and Tolerability of the Lidocaine Patch 5%, . . . . The Journal of Clinical Pharmacology, 43: 111-117.
Leppert et al., 2018. "Transdermal and Topical Drug Administration in the Treatment of Pain" Molecules 23, No. 3: 681.
Elhafz et al. Anesthesia: Essays and Researches, vol. 6, No. 2, Jul.-Dec. 2012, p. 140.
Sandeep Nema, R.J. Washkuhn and R.J. Brendel. "Excipients and Their Use in Injectable Products" PDA J Pharm Sci and Tech 1997, 51 166-171. Showa Denko, (n.d.), Pharmaceutical excipient for external use VISCOMATE, [Brochure].

\* cited by examiner

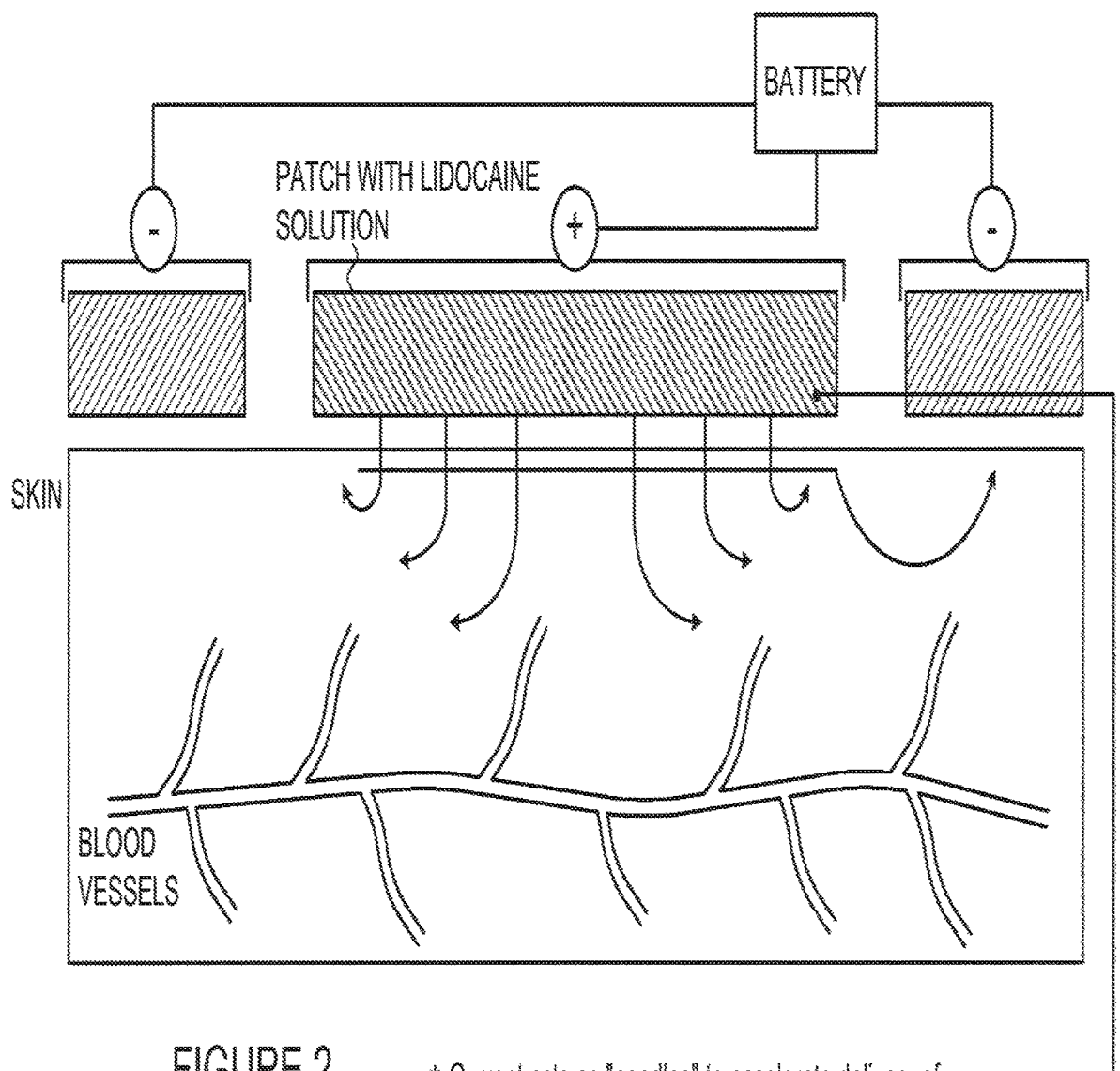
FIGURE 2.   * Current acts as "needles" to accelerate delivery of analgesic compound

LIDOCAINE PATCH AND METHODS OF USE THEREOF

CROSS REFERENCED TO RELATED APPLICATIONS

This application claims benefit of the U.S. Provisional Application Ser. No. 61/578,264 filed Dec. 21, 2011, hereby incorporated by reference to its entirety.

FIELD OF INVENTION

This invention is directed to a transdermal delivery patch comprising a local analgesic agent and optionally a permeation enhancement agent, for reducing pain.

BACKGROUND OF THE INVENTION

It is known that neuropathic pain including back pain, diabetic nerve pain, complex regional pain syndrome type II (CRPS-II), carpal tunnel syndrome, phantom limb pain, chemotherapy-induced neuropathy, or HIV sensory neuropathy and other nerve pain disorders have a predominantly neurological cause.

Presently, the symptoms of pain are predominantly treated pharmacologically with systemically active, oral or injectable analgesics and antiphlogistics, and, in part, in combination with psychosomatic or physical therapy, sometimes also in combination with other methods, such as, acupuncture. The last resort for diseases causing neuropathic pain, such as those of the intervertebral disk, is surgery.

An oral analgesic is carried into the patient's circulatory system and prevents the recognition of pain systemically by interrupting the transmission of pain signals from sensory neurons to the pain centers in the brain. Traditional oral analgesics include opioids (narcotics) such as morphine, codeine, methadone, Demerol® (meperidine hydrochloride) or Darvon® (propoxyphene hydrochloride); and non-steroidal anti-inflammatory drugs (NSAIDs), such as aspirin, ibuprofen or naproxen.

The systemic use of these drugs carries patient risk. Opioid use causes a variety of undesired side-effects, including sedation, dizziness, depression, nausea and constipation. Prolonged opioid usage carries a risk of patient addiction. The large and sometimes prolonged doses of non-steroidal anti-inflammatory drugs ("NSAIDs") required to treat intense pain can cause gastric disorders, erosion of the stomach lining and intestinal mucus membrane, nephrotoxicity, hepatotoxicity, as well as internal bleeding. Orally administered drugs also cause side-affects that restrict physical activity (primarily in the case of opioids, due to sedation) and inhibit effective physical therapy.

In addition, neuropathic pain is often resistant to available drug therapies; a hallmark of neuropathic pain is its intractability. Typical non-steroidal anti-inflammatory drugs (NSAIDs) such as aspirin, indomethecin, and ibuprofen do not relieve neuropathic pain. The neuropathic pain observed in animal models predictive of human clinical outcome does not respond to NSAIDs.

Unfortunately, all systemic analgesics have a considerable number of undesirable side effects in common. The salicylic acid derivatives and nonsteroidal antiphlogistics are associated considerably and frequently with gastric disorders as a result of the antiproliferative active mechanism. Paracetamol, with a weaker effect, is associated with metabolic stress of liver and kidney functions, especially when used for a prolonged period of time and at required higher doses. Therefore, application of these therapies is limited by the spectrum of undesirable, product-specific effects in each case, because systemic interventions involve all of the organs and the organ systems. In addition, therapies such as surgery, in themselves present significant medical risks to the patient. These pharmacotherapies, do not represent sufficiently tolerable and effective forms of treatment.

Pain can also be treated locally by delivering a pain reliever directly to the site of pain or in a region near or surrounding the site of pain, through use of a local anesthetic.

Systemic application of local anesthetics might be applied invasively by means of injection. However, this option is practically eliminated due to the danger of systemic overdosage with, among others, serious cardiac side effects. Direct application of local anesthetics through local injection is technically possible and is performed in different ways. However, local injections are not only painful, but can also never be done directly by the patient. The local surface injection technique involves so-called neural therapy with muscular trigger points and requires experienced medical handling and technique (J. T. Travell, D. G. Simons, Myofascial Pain and Dysfunction, Vol. I/II, Williams & Wilkins, Baltimore, 1983). Therefore, this option is limited to use in clinically severe disorders. There is also the drawback that a local anesthetic injected into a highly vascularized area of the body can be carried away by the circulatory system and create the same risks as systemically administered anesthetics. This risk is increased when local anesthetic dosages are increased to manage intense pain. Further, use of conventional topical formulations, for example, creams, allows neither exact dosage nor continuous penetration over a prolonged period of application.

The topical administration of a local anesthetic overcomes some of the drawbacks of injection. There is no need for the painfully invasive procedure and professional administration is not needed. The risk of the locally applied anesthetic acting as a systemically administered drug also is much reduced.

Dermal patches are well known to administer local anesthetics topically to patients at wound sites and to treat skin ailments. Dermal pain patches have a number of benefits, not the least of which is convenience. Amide and ester group-containing, for example, lidocaine of the amide type, exhibit, as a pharmacological active mechanism, an inhibition of the rapid sodium ion influx in nerve fibers. In this manner, the impulse conduction of the nerve path is blocked, which in principle involves all regional nerve fibers.

A prescription strength 5 percent lidocaine patch marketed as Lidoderm® (lidocaine patch 5%) is available from Endo Pharmaceuticals, Inc. The patch may make the patient warmer, and thus be a burden in hot environments. Moreover, an overdose of lidocaine can cause fatal side effects if too much lidocaine is absorbed through your skin and into your blood.

A more effective pharmacological principle might be a suitable form of low-dosed local analgesics delivered in a dermal patch. It is therefore an object of the present invention to provide a low-dosage topical dermal patch comprising lidocaine that can be used to provide relief from neuropathic pain over a period of time.

Given the high incidence of neuropathic pain and its effect on the general population, new innovative remedies are needed to reduce pain in a subject. Advantageous remedies include those that can be applied locally, do not cause negative side-effects, are easy for a patient to apply, do not require professional administration or painful injections and allow a single administration to treat one or more pain sites for a prolonged period of time.

SUMMARY OF THE INVENTION

In one embodiment of the present invention, a patch for transdermal delivery of lidocaine for reducing pain, including neuropathic pain, osteoarthritis pain, back pain, pain from fibromyalgia, pain from muscle strains, pain from muscle sprains or degenerative bone pain or any combination thereof, comprises a patch comprising a composition comprising a therapeutically effective amount of lidocaine, wherein the amount of lidocaine is less than 4 percent by weight.

In one embodiment, the composition further comprises a treatment enhancing amount of a permeation enhancement agent. In another embodiment, the permeation enhancement agent is menthol. In yet another embodiment, the amount of menthol is up to 16 percent by weight. In still another embodiment, the amount of menthol is between about 3 to 5 percent.

In one embodiment of this invention, the therapeutically effective amount of lidocaine is 3.95 percent by weight.

In one embodiment, the lidocaine may be a pharmaceutically acceptable lidocaine base.

In one embodiment, the methods of this invention include reducing pain, including neuropathic pain, osteoarthritis pain, back pain, pain from fibromyalgia, pain from muscle strains, pain from muscle sprains or degenerative bone pain or any combination thereof, in a subject comprising applying on a skin surface of the subject at or near the site of pain, a patch comprising a composition comprising a therapeutically effective amount of lidocaine, wherein the amount of lidocaine is less than 4 percent by weight, and wherein application of the patch provides transdermal delivery of an amount of lidocaine sufficient to reduce the pain in the subject.

In one embodiment, the patch is applied for about 8 to 12 hours.

In one embodiment, methods of this invention provide that application of a patch of this invention reduces neuropathic pain including back pain, diabetic neuropathic pain, nerve compression or nerve trauma, or any combination thereof.

In one embodiment, methods of this invention include compositions further comprising a treatment enhancing amount of a permeation enhancement agent. In one embodiment, methods include the use of menthol as a permeation enhancement agent. In one embodiment, the amount of method used in a method of this invention is up to 16 percent by weight. In one embodiment the amount of menthol used in a method is between about 3 to 5 percent by weight.

In one embodiment, the methods of this invention employ a therapeutically effective amount of lidocaine, wherein that amount is 3.95 percent by weight.

In one embodiment of the invention, the lidocaine employed in a method of this invention is its pharmaceutically acceptable salt, free base or any combination thereof. In another embodiment of the invention, the lidocaine employed in a method of this invention is its pharmaceutically acceptable free base.

In one embodiment, methods of this invention reduce pain for at least 12 hours. In another embodiment, methods reduce pain for at least 24 hours. In yet another embodiment, methods reduce pain for more than 24 hours.

In some embodiments, methods of this invention include an additional step for enhanced delivery of said lidocaine. In one embodiment, methods include the use of iontophoresis, a battery powered electronic stimulant or magnetophoresis for enhanced deliver of an active ingredient, e.g., lidocaine.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which

FIG. 2 illustrates delivery of a medication, e.g., a lidocaine solution, into the skin using iontophoresis.

DETAILED DESCRIPTION OF THE PRESENT INVENTION

Figure 1:
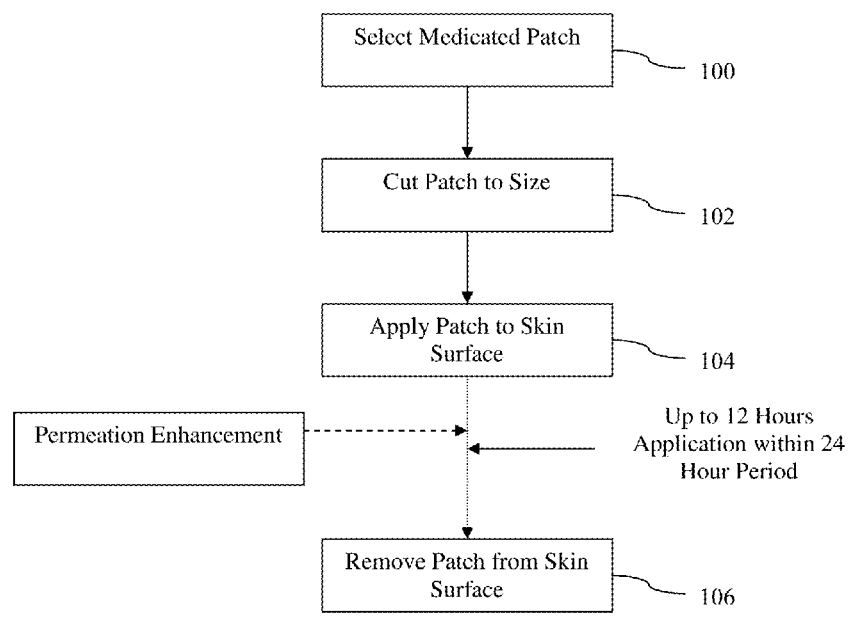
FIG. 1 is a schematic block diagram of a method of reducing neuropathic pain in a subject, in accordance with embodiments of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention is directed to a patch for transdermal delivery of lidocaine for reducing pain, including neuropathic pain, osteoarthritis pain, back pain, pain from fibromyalgia, pain from muscle strains, pain from muscle sprains or bone degeneration pain or any combination thereof, comprising a composition comprising a therapeutically effective dosage of lidocaine and methods of use thereof.

The patch of the present invention may be used to reduce neuropathic pain, including back pain and/or discomfort. In addition, the patch of the present invention may be used to reduce osteoarthritis pain, pain from fibromyalgia, pain from muscle strains, pain from muscle sprains or bone degeneration pain or any combination thereof. The patch of the present invention may, in addition to a dosage of lidocaine, include treatment enhancing amounts of a permeation enhancement agent. The present invention may be used to reduce pain for extended time periods, e.g., 24 hours. The patch and methods of use thereof according to the present invention may be better understood with reference to the drawing and accompanying descriptions.

Before explaining at least one embodiment of the present invention in detail, it is to be understood that the invention is not limited in its application to the details of construction and the arrangement of the components as set forth in the following description or illustrated in the drawing. The invention is capable of other embodiments or of being practiced or carried out in various ways. Also, it is to be understood that the phraseology and terminology employed herein are for the purpose of description and should not be regarded as limiting.

I. Definitions

As used herein, the term "patch" refers to a medicated patch, e.g., a patch, comprising a composition comprising at least one active ingredient that is placed on the skin to deliver a continuous dosage of the active ingredient through the skin and into the surrounding tissue. In one embodiment, the active ingredient may penetrate deeply below the skin to a site of pain for deep tissue pain relief. In one embodiment, the active ingredient penetrates just below the skin to a site of pain localized therein for local pain relief. In one embodiment, the continuous dosage of the active ingredient provides minimal entry of the active ingredient into the blood stream. In another embodiment, the continuous dosage provides no entry of the active ingredient into the blood stream.

As used herein, the term "patch" may also be referred to herein as a "topical delivery system", a "topical patch delivery system", an "adhesive patch", a "transdermal patch", a "transdermal delivery system", an "analgesic patch", a "dressing", a "topical carrier system".

Transdermal patches are a well-accepted technology used to deliver a wide variety of pharmaceuticals. Patches of the present invention may be placed on the skin for specified therapeutic time periods and remain in place for up to 12 hours. Therapeutically effective dosages of pharmaceuticals are the choice for use with a patch of this invention.

Patches may comprise an adhesive to remain in place when placed on the skin or may be adhered by other means including adhesive tape or strips. In addition, patches of the present invention may be perforated and/or stretchable in order that they may be wrapped around an appendage or body part. In certain embodiments, a stretchable patch may be wrapped fully around an appendage or body part. In alternative embodiments, a stretchable patch may be wrapped partly around an appendage or body part. For example a patch of the present invention may be wrapped around a knee, ankle, leg, elbow, wrist, finger, arm or neck. By wrapping the patch, pain relief may be provided at sites recalcitrant to a patch that would otherwise be expected to remain in place using just an adhesive, for example a moving joint such as an elbow, knee or wrist joint.

In one embodiment, the patch is an adhesive patch. In another embodiment, the patch is not adhesive. In yet another embodiment, the patch may be wrapped around a bodily appendage. In still another embodiment, the patch may be both adhesive and able to be wrapped around an appendage.

Conventional dermal patches include a carrier that holds a drug and allows the drug to be released onto a patient's skin for absorption. Many different kinds of dermal patches are known, including matrix type patches, reservoir-type patches, multi-laminate drug-in-adhesive type patches, and monolithic drug-in-adhesive type patches, and many others. Such patches can be readily prepared using technology which is known in the art such as described in Remington's Pharmaceutical Sciences, 18$^{th}$ or 19$^{th}$ editions, published by the Mack Publishing Company of Easton, Pa.

Patches of the present invention may include: (1) a backing layer, having an adhesive thereon; (2) an analgesic component for delivery of the analgesic, preferably, an analgesic in a carrier, referred to herein as an "analgesic composition" or "composition"; wherein the analgesic components are collectively referred to herein as the "active components" or "active ingredients". These components are described in more detail below. In another embodiment, the analgesic composition comprises lidocaine.

Patches of the present invention can be any shape or size or can be customized to fit irregularly shaped body parts associated with pain, e.g., joints, back, neck, arms, legs, shoulders, hips, wrists, ankles, knees and/or fingers. For example, patches of the invention can be rectangular, square, round or oval in shape. Patches may also be perforated and stretchable for wrapping around different body appendages and/or joints, e.g., arms, legs, wrists, ankles, knees and/or fingers. Varying the size of the patch used varies the dosage. Often a patch is cut and only a portion is used. In some instances, the use of more than one patch may be advisable.

In one embodiment, patches are 10 cm×14 cm. In another embodiment, patches are smaller than 10 cm×14 cm. In yet another embodiment, patches are larger than 10 cm×14 cm.

In one embodiment, patches are cut to the size and shape needed for use in pain reduction. In one embodiment, the patch remains intact while the size of the patch changes upon stretching.

Patches suitable for use in the present invention include, but are not limited to, (1) the matrix patch; (2) the reservoir patch; (3) the multi-laminate drug-in-adhesive patch; and (4) the monolithic drug-in-adhesive patch; as described in Transdermal And Topical Drug Delivery Systems, pp. 249-297 (Tapash K. Ghosh et al. eds., 1997), hereby incorporated in full herein by reference. These patches are well known in the art and generally available commercially.

The matrix patch comprises a drug containing matrix, an adhesive backing film overlay, and preferably, a release liner. In some cases, it may be necessary to include a impermeable layer to minimize drug migration into the backing film (e.g., U.S. Pat. No. 4,336,243, incorporated in full herein by reference). The drug-containing matrix is held against the skin by the adhesive overlay. Examples of suitable matrix materials include, but are not limited to, lipophilic polymers, such as polyvinyl chloride, polydimethylsiloxane, and hydrophilic polymers like polyvinylpyrrolidone, polyvinyl alcohol, hydrogels based on gelatin, or polyvinylpyrrolidone/polyethylene oxide mixtures.

The reservoir type patch design is characterized by a backing film coated with an adhesive and a reservoir compartment comprising a drug formulation, preferably in the form of a solution or suspension that is separated from the skin by a semipermeable membrane (e.g., U.S. Pat. No. 4,615,699, hereby incorporated in full herein by reference). The adhesive coated backing layer extends around the reservoir's boundaries to provide a concentric seal with the skin and hold the reservoir adjacent to the skin.

The monolithic/single drug-in-adhesive patch design is characterized by the inclusion of the drug formulation in the skin contacting adhesive layer, a backing film, and preferably, a release liner. The adhesive functions both to release the analgesic and adhere the analgesic matrix to the skin. The drug-in-adhesive system does not require an adhesive overlay and thus the patch size is minimized. Also, drug-in-adhesive type patches are thin and comfortable (e.g., U.S. Pat. No. 4,751,087, incorporated in full herein by reference).

The multi-laminate drug-in-adhesive patch design further incorporates an additional semi-permeable membrane between two distinct drug-in-adhesive layers or multiple drug-in-adhesive layers under a single backing film. See Peterson, T. A. and Dreyer, S. J. 21 Proceed. Intern. Symp. Control. Rel. Bioact. Mater. 477-478 (Nice, France 1994), hereby incorporated in full herein by reference).

The backing layer or backing serves as the upper surface of the patch and functions as the primary structural element and provides the patch with its flexibility. The material selected for the backing material should be selected so that it is substantially impermeable to the local analgesic and any other materials present; the backing is preferably made of a sheet or film of a flexible elastomeric material. The backing supports the active layers by way of an adhesive and holds the active layers against the application site. The combination of backing and adhesive should be biocompatible, non-irritating to the skin, breathable and able to hold the patch thinly against the skin.

Backings for use in patches of the invention are preferably made of a flexible, biocompatible material that imitates the elastic properties of skin and conforms to the skin during movement. Preferred have a moisture-vapor transmission rate similar to human skin. This reduces the chance of an infection developing under the patch after it is applied to a patient's skin.

Preferably, the backing layer is derived from synthetic polymers like polyolefin oils polyester, polyethylene, polyvinylidine chloride, and polyurethane or from natural materials like cotton, wool, etc. Non-occlusive backings allow the area to breathe (i.e., promote water vapor transmission from the skin surface). In one embodiment, the backing film is an occlusive polyolefin foil (Alevo, Dreieich, Germany). The polyolefin foil is preferably about 0.6 to about 1 mm thick. Other suitable backings are commercially available; for example, suitable backings can be purchased from 3M (St. Paul, Minn.) and Bertek (St. Albans, Vt.).

In one embodiment, the patch includes an occlusive dressing. In another embodiment, the patch includes a non-occlusive dressing. For example, a non-occlusive patch can enable moisture vapor on the surface of the skin to evaporate through the patch so as to prevent the undesired accumulation of moisture which, if it occurred, could cause the patch to fall off or even facilitate the growth of bacteria beneath the patch.

Permeable membranes can be used with patches of the present invention to overlay the portion of the patch adjacent to the skin to permit delivery of the patch's active ingredients to the application site. Preferably, the permeable membrane comprises a breathable material that is agreeable to the surface of a surgically closed wound and permits local delivery of local anesthetic into the skin of the patient at the wound site. Permeable membranes permit controlled delivery of the active components of the patch.

Permeable membranes useful in the present invention include thin non-porous ethylene vinyl acetate films or thin micro-porous films of polyethylene and polypropylene. Preferably, the permeable membrane is an ethyl vinyl acetate copolymer membrane. Suitable permeable membranes are commercially available; for example, suitable permeable membranes can be purchased from 3M (St. Paul, Minn.)

Adhesives may be used with patches of the present invention to adhere the active components to the backing and to adhere the backing to the patient's application site. Preferably, adhesives useful in the present invention can function under a wide range of conditions, such as, high and low humidity, bathing, sweating etc. Adhesives for use with patches of the present invention are well known in the art and selection is readily accomplished by an ordinary practitioner. Suitable adhesives include, but are not limited to, polyisobutylene-based adhesives, silicone-based adhesives, and acrylic-based adhesives. Preferably the adhesive is a composition based on natural or synthetic rubber; a polyacrylate such as, polybutylacrylate, polymethylacrylate, poly-2-ethylhexyl acrylate; polyvinylacetate; polydimethylsiloxane; and hydrogels (e.g., high molecular weight polyvinylpyrrolidone and oligomeric polyethylene oxide). Patches of the present invention deliver their medicine directly to the site of a person's pain. This may eliminate some of the side effects that come with oral dosing or local injections. For instance, some analgesics are likely to cause an upset stomach unless they're taken with food. And, because patches of the present invention provide minimal release of their active ingredient into the blood stream and provide release of their active ingredient slowly into the body tissues through the skin, people should also get more consistent pain relief than they do with oral dosing or injections.

The composition of the present invention is a pharmaceutical composition. The pharmaceutical composition of the invention includes pharmaceutically acceptable carriers.

As used herein, the terms "pharmaceutically acceptable carrier", "carrier", or "vehicle" refers to carrier materials suitable for transdermal drug administration. Carriers and vehicles useful herein include any such materials known in the art which are nontoxic and do not interact with other components. As used herein the term "a pharmaceutically acceptable carrier" refers to any substantially non-toxic carrier conventionally useable for transdermal administration of pharmaceuticals in which an active ingredient will remain stable and bioavailable. In one embodiment of the present invention, the local-analgesic of the composition of the present invention comprises a pharmaceutically acceptable carrier to contain and deliver the active component to the application site. As used herein, the term "carrier" may herein be interchangeable with the term "patch"

In certain embodiments, carriers are sterile and pharmaceutically acceptable for topical application and delivery of an active ingredient into or through a patient's skin. Preferred functional characteristics of carriers are low adhesive strength, breathability, and conformability to the application area.

Pharmaceutically acceptable carriers for use in the invention are standard in the art, for example, matrix-type carriers, reservoir-type carriers, multi-laminate-type carriers, and monolithic drug-in-adhesive type carriers, such as those disclosed in "Transdermal And Topical Drug Delivery Systems" (Tapash K. Ghosh et al. eds., 1997); see also Kristine Knutson and Lynn K. Pershing, Topical Drugs, in Remington: The Science And Practice Of Pharmacy 866-885 (Alfonso R. Gennaro ed., 1995), the disclosures of which is hereby incorporated herein in full by reference.

In a preferred embodiment, the carrier is a matrix-type drug carrier. Matrix-type drug carriers are well known in the art. Suitable matrix-type drug carriers include, but are not limited to, the adhesives discussed below, such as polyisobutylene-based adhesives, silicone-based adhesives, and acrylic-based adhesives.

In another embodiment, the carrier is a hydrogel. Hydrogels are a mixture of water and a gelling agent, such as a hydrophilic polymer. In general, hydrogels form a three-dimensional lattice of polymer chains that retains an aqueous solution in a flexible, stable shape. Preferred hydrogels contain gelling agents distributed substantially uniformly throughout the carrier liquid, which is typically aqueous and may contain an alcohol and/or an oil.

Preferred gelling agents include, but are not limited to, crosslinked acrylic acid polymers such as carboxypolyalkylenes; hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Suitable hydrogels are commercially available, for example, suitable hydrogels can be purchased from BASF (St. Paul, Minn.) or Noveon (Cleveland, Ohio).

As used herein, the term "active ingredient" refers to a suitable drug that provides local analgesia or deep tissue analgesia, or a combination thereof, or a drug that provides a regional blockage of nervous pathways that carry pain signals. As used herein, the term "active ingredient" may also be referred to as "drug" or "active component".

As used herein, the term "analgesia" refers to a neurological or pharmacological state characterized by an absence of normal sensibility to pain, without an effect on consciousness. Accordingly, painful stimuli are either not perceived at all, or they are moderated such that, even though they may still be perceived, they are no longer painful.

In one embodiment, an active ingredient may act as an analgesic. The analgesic may operate as a local analgesic and/or penetrate deeper and enter the blood stream. In one embodiment, the active ingredient functions as a local analgesic. In another embodiment, the active ingredient functions as an analgesic for deeper tissue. In yet another embodiment, the active ingredient does not enter the blood stream. In another embodiment, the active ingredient only minimally enters the blood stream.

In one embodiment, administration of a patch comprising a composition comprising the active ingredient, acts to reduce pain, including neuropathic pain, osteoarthritis pain, back pain, pain from fibromyalgia, pain from muscle strains, pain from muscle sprains or bone degeneration pain or any combination thereof, in a subject.

As used herein, the term "reducing pain" refers to alleviating pain localized at a site of interest. The reduction of pain may include alleviating pain in an area around the site of interest.

As used herein, "pain," includes both acute pain and chronic pain, which may be centralized pain, peripheral pain, or combination thereof.

As used herein, the term "acute pain" refers to centralized or peripheral pain that is intense, localized, sharp, or stinging, and/or dull, aching, diffuse, or burning in nature and that occurs for short periods of time.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring).

As used herein, the term "neuropathic pain" refers to any and all types of neuropathic pain regardless of the cause. Neuropathic pain refers to pain that originates from pathology of the nervous system. Neuropathic pain reflects both peripheral and central sensitization mechanisms.

Abnormal signals arise not only from injured axons but also from the intact nociceptors that share the innervation territory of the injured nerve. Neuropathic pain may result from lesions of the central nervous system, or from the peripheral nervous system. Neuropathic pain may also arise from disorders of ion channels, such as the sodium channels. The nervous system can generate and perpetuate pain (i.e., neuropathic), without any ongoing stimuli from injury. Neuropathic pain is often puzzling and frustrating for both patients and physicians because it seems to have no cause, responds poorly to standard pain therapies, can last indefinitely and even escalate over time, and often results in severe disability. The reduction of neuropathic pain as described herein refers to the alleviation or elimination of the neuropathic pain associated with a neuropathy.

Four pathological mechanisms are associated with the generation of pain in peripheral tissues in neuropathic pain conditions. These are: 1) nociceptor sensitization, whereby nociceptors have enhanced sensitivity to stimuli; 2) spontaneous activity related either to abnormal activity of transduction channels, or abnormal sensitivity of spike generation mechanisms; 3) abnormal coupling between sympathetic efferent fibers and nociceptors (sympathetically maintained pain); and 4) deafferentation, a central mechanism of pain whereby pain results from abnormal activity in neurons concerned with pain in the central nervous system as a result of altered input from primary afferents.

The primary sensory neurons that carry signals related to pain are called C-fiber and A-delta nociceptors. Normally, they fire action potentials in response to noxious mechanical, thermal, and/or chemical stimuli. Lumbar disk herniation with its accompanying chemical irritants to the adjacent nerve root can produce sciatic nerve pain. Carpal tunnel syndrome is due to a combination of repetitive stretching of the median nerve, compression caused by edema and hypertrophy of surrounding tissues, and inflammation producing chemical irritation of the median nerve. Trigeminal neuralgia has been attributed to vascular compression on the trigeminal nerve near the brain stem and may also relate to conditions such as multiple sclerosis.

Nerve fibers that have been damaged by injury or disease can fire spontaneously at the site of injury or at ectopic foci along the damaged nerve. Resulting paroxysms of pain are often described as lancinating, stabbing, or shooting. It is believed that when many nerve fibers are affected and fire asynchronously, neuropathic pain has a quality of continuous burning results. In addition however, the nerve fibers that share the innervation territory of the injured nerve can also discharge abnormally. This discharge arises in the skin and therefore lends itself to topical therapy. Clonidine applied topically has been discovered to relieve pain after delivery to the painful site, for example.

Under normal conditions, sensations are transmitted from peripheral tissues via a connected chain of neurons in the spinal cord, brain stem, and brain. Interruption of any portion of that chain provides the potential for increased irritability and firing of nerves further up the pathway. This phenomenon explains how phantom limb pain can occur. Loss of sensory input from a limb can produce spontaneous firing of second- and third-order neurons, resulting in pain and other sensory experiences in the missing limb. Similarly, nerves damaged by diabetic neuropathy, post-herpetic neuropathy, or peripheral nerve trauma may generate firing in the higher-order nerves and, thus, ongoing pain.

Examples of specific sources of neuropathic pain for which the methods of the present invention can be used include autoimmune diseases, e.g., multiple sclerosis; metabolic diseases, e.g., diabetic neuropathies; back pain, spine or back surgery; postherpetic neuralgia; vascular disease; trauma; complex regional pain syndrome type II (CRPS-II); carpal tunnel syndrome; phantom limb pain; chemotherapy-induced neuropathy; central pain syndrome; trigeminal neuralgia; reflex sympathetic dystrophy syndrome; nerve compression; stroke; spinal cord injury; or HIV sensory neuropathy, or other nerve pain disorders having a predominantly neurological cause.

In contrast to feelings of immediate pain upon tissue injury, neuropathic pain can develop days or months after a traumatic injury. Furthermore, while pain caused by tissue injury is usually limited in duration to the period of tissue repair, neuropathic pain frequently is long lasting or chronic.

Moreover, neuropathic pain can occur spontaneously or as a result of stimulation that normally is not painful.

As used herein, the term "osteoarthritis pain" refers to pain associated with a degenerative joint disease where the cartilage that normally cushions the joint and protects it from impact erodes.

As used herein, the term "pain from fibromyalgia" refers to pain associated with a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, the term "back pain" refers to pain associated with all regions of the back including lower, mid and upper back pain.

As used herein, the term "bone degeneration pain" refers to pain associated with conditions leading to degenerative bone disorders characterized by low bone mass and microarchitectural deterioration of bone tissue, leading to enhanced bone fragility and increased fracture risk.

As used herein, the term "pain from muscle strains" refers to pain associated with muscle tears and/or pulled muscles. Muscle strains occur when an excessive amount of force or pressure is directed onto muscles that cause damage or tearing to the muscle fibers and/or surrounding tendons. common muscle strains, torn muscles and pulled muscles are: Achilles tendon tear, pulled backs, lower back muscle strain, tearing the rotator cuff, abs (abdominal) muscle strains, calf muscle strain, hamstring muscle strain, quads (quadriceps) muscle strain, leg muscle strain, knee (or plantaris) muscle strain, chest muscle strain, groin pull or muscle strain, bicep muscle strain, and arm muscle strain.

As used herein, the term "pain from muscle sprains" refers to pain associated with a stretch or tear of a ligament, the band of connective tissues that joins the end of one bone with another. Sprains are caused by trauma such as a fall or blow to the body that knocks a joint out of position and, in the worst case, ruptures the supporting ligaments.

The patches of the present invention can be used to reduce pain such as neuropathic pain. For example, the patches of the present invention may be used to reduce pain associated with diabetic neuropathy, back pain, carpel tunnel syndrome or other pains associated with nerve injury or any combination thereof. In addition, the patches of the present invention may also be used to reduce pain associated with fibromyalgia, muscle strains, muscle sprains, osteoarthritis or bone degeneration or any combination thereof.

Compositions of this invention are described below. In some embodiments, any of the compositions of this invention will comprise lidocaine, in any form or embodiment as described herein. In some embodiments, any of the compositions of this invention will comprise a combination of lidocaine and menthol, in any form or embodiment as described herein. In some embodiments, any of the compositions of this invention will consist of lidocaine, in any form or embodiment as described herein. In some embodiments, any of the compositions of this invention will consist of a combination of lidocaine and menthol, in any form or embodiment as described herein. In some embodiments, any of the compositions of this invention will consist essentially of lidocaine, in any form or embodiment as described herein. In some embodiments, any of the compositions of this invention will consist essentially of a combination of lidocaine and menthol, in any form or embodiment as described herein. The term "comprise" refers to the inclusion of the indicated active agents, such as the a combination of lidocaine and menthol, as well as inclusion of other active agents, and pharmaceutically acceptable carriers, excipients, emollients, stabilizers, etc., as are known in the pharmaceutical industry. The term "consisting essentially of" refers to a composition, whose only active ingredients are the indicated active ingredients, however, other compounds may be included which are for stabilizing, preserving, etc. the formulation, but are not involved directly in the therapeutic effect of the indicated active ingredients. The term "consisting essentially of" may refer to components which facilitate the release of the active ingredients. The term "consisting" refers to a composition, which contains the active ingredient and a pharmaceutically acceptable carrier or excipient.

As used herein, the term "transdermal delivery" refers to the delivery of a compound, e.g., an active ingredient of this invention or other therapeutic agent, through one or more layers of the skin (e.g., epidermis, dermis, etc). Transdermal delivery of an active ingredient of this invention, e.g., lidocaine, may include administration of the active ingredient to the skin surface of a subject, including a human subject, so that the active ingredient passes through the skin tissue and, for example, into deeper tissue thereby providing deep tissue relief of pain.

Administration of the active ingredient or compositions of this invention includes topical administration. As used herein, the term "topical" refers to administration of a patch of this invention at the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. Ideally, the substance will not reside in the skin for any extended period of time, but will penetrate into localized tissue, deep tissue and/or synovial fluids in order to provide localized, deep tissue or "joint" pain relief or any combination thereof. In one embodiment, transdermal delivery is enhanced, wherein enhancement may be through chemical or physical means.

As used herein, the term "therapeutically effective amount" refers to that amount of any active ingredient, e.g., lidocaine, which provides a therapeutic or beneficial effect for a given condition and administration regimen to a subject. The concentration of the substance is selected so as to exert its pharmaceutical effect at dosages. In certain circumstance, such dosages are low enough to avoid significant side effects to a subject. The effective amount of an active ingredient may vary with the particular site at which a patch of this invention is placed, e.g., the thickness of the skin tissue at the treatment site, the age and physical condition of the biological subject being treated, the severity of the condition, the duration of the treatment, the nature of concurrent therapy, the specific compound, composition or other active ingredient employed, the particular carrier utilized, and like factors. The effective amount of any of the active ingredients comprised in the compositions of the present invention may, for example, be the amount that results in a therapeutic or beneficial effect following its administration to a subject. The concentration of an active ingredient is selected so as to exert its pharmaceutical effect, but low enough to avoid significant side effects within the scope and sound judgment of the skilled artisan. The effective amount of the composition may vary with the particular epithelial tissue being treated, the age and physical condition of the biological subject being treated, the severity of the condition, the duration of the treatment, the nature of concurrent therapy, the specific compound, composition or other active ingredient employed, the particular carrier utilized, and like factors. As used herein, the term "therapeutically effective amount" may also be referred to herein as a "pharmaceutically effective amount".

As used herein, the term "permeation enhancement" refers to enhancement of the percutaneous penetration of the active ingredient, allowing for a fast onset of action. As used herein, the term "permeation enhancement" may also be referred to as "transdermal enhancement" or "penetration enhancement". In one embodiment, permeation enhancement may be performed through the use of chemical permeation enhancers. In another embodiment, permeation enhancement may be performed through the use of physical permeation enhancers. Physical permeation enhancer techniques include magnetophoresis, iontophoresis or a battery powered electronic stimulant.

Iontophoresis, also known as Electromotive Drug Administration (EMDA), is a technique using a small electric charge to deliver a medicine, drug, active ingredient or other chemical through the skin. It may function similar to an injection without the needle, for example EMDA may be used for localized entry of a drug into the skin. In addition, EMDA may be used for concentrated application of a medication under the skin (FIG. 2). As used herein, "iontophoresis" refers to a non-invasive method of propelling high concentrations of a charged substance, for example a medication, a drug, an active ingredient or a bioactive agent, transdermally by repulsive electromotive force using a small electrical charge applied to an iontophoretic chamber containing a similarly charged active agent and its vehicle. One or two chambers may be filled with a solution containing an active ingredient and its solvent, also called the vehicle. The positively charged chamber, called the anode, will repel a positively charged chemical, whereas the negatively charged chamber, called the cathode, will repel a negatively charged chemical into the skin.

Iontophoresis is well known for use in transdermal drug delivery. Unlike transdermal patches, this method relies on active transportation within an electric field. In the presence of an electric field electromigration and electroosmosis are the dominant forces in mass transport. These movements are measured in units of chemical flux, commonly μmol/cm2h. As described herein, iontophoresis may be used in conjunction with a patch of this invention for "permeation enhancement" of an active ingredient (FIG. 2).

At the same time, the active ingredient must not penetrate so effectively through the skin as to be rapidly lost to the systemic circulatory systems, as shown for example in FIG. 2 where the lidocaine solution is not entering the blood stream. Thus, the ideal vehicle would also enhance the skin's ability to retain the pharmacologically active ingredient or, in other words, to increase skin residence times.

As used herein, the term "pain-relieving amount" refers to the amount of any of the active ingredients of this invention that results in the reduction of pain following its administration to a subject.

As used herein, the term "subject" refers to all animals including humans. Examples of patients or subjects include humans, cows, dogs, cats, goats, sheep, and pigs. As used herein, the term "subject" may also be referred to as a "patient".

The terms "treating" or "treatment" includes, but is not limited to, the application of the patch comprising a composition comprising at least on active ingredient to the skin of a patient to prevent, reduce or inhibit the sensation of pain in the vicinity or region of the application of the patch.

Further, the terms "treating" or "treatment" as used herein refer to reducing in severity and/or frequency of symptoms and/or their underlying cause of neuropathic pain.

II. Patches for Pain Reduction

The present invention provides patches comprising a low-dose lidocaine pharmaceutical composition, wherein the lidocaine may act as an analgesic. In this way, the lidocaine can provide a regional blockage of nervous pathways that carry pain signals, thereby reducing pain suffered by a subject. As used herein, the term "low-dose" refers to an amount of lidocaine less than 5% by weight. In another embodiment, the term "low-dose" refers to an amount of lidocaine less than 4% by weight.

As used herein, "pharmaceutical composition" means a "therapeutically effective amount" of the active ingredient, e.g., lidocaine, together with a pharmaceutically acceptable carrier or diluent. The pharmaceutical compositions of the present invention may be a sustained or extended release composition or an immediate release composition comprising lidocaine. An example of a pharmaceutical composition of this invention includes a therapeutically effective amount of lidocaine in a physiologically acceptable vehicle. As used herein the tem "pharmaceutical composition" may also be referred to herein as a "composition". The methods to prepare the compositions useful in the present invention are within the ordinary skill of persons in the art.

In one embodiment, a composition of this invention is administered to reduce the intensity of pain in a subject.

In one embodiment, this invention provides a patch for transdermal delivery of lidocaine for reducing pain comprising, a patch comprising a composition comprising a therapeutically effective amount of lidocaine, wherein the amount of lidocaine is less than 4 percent by weight. As used herein, the term "lidocaine" may also be referred to herein as the "analgesic" or "local analgesic".

The patches of this invention employ lidocaine as an active ingredient in a form capable of transdermal transport into the dermis or deeper. In one embodiment, the lidocaine can be formulated at least in part, as the free base. In another embodiment, lidocaine active ingredients can be formulated as neutralized pharmaceutically acceptable salt forms. Pharmaceutically acceptable salts include the acid addition salts, which are formed with inorganic acids such as, for example, hydrochloric, sulfuric or phosphoric acids, or such organic acids as acetic, oxalic, tartaric, mandelic, citric and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The patch delivery system of this invention comprises a composition comprising a low-dose of lidocaine. As used herein, the terms "dose" or "dosage" refer to the measured quantity of an active ingredient administered at one time. As used herein, the term "dosage" may also herein be referred to as "dose" or "amount". In one embodiment, the composition comprises less than 4 percent lidocaine by weight. In one embodiment, the amount of lidocaine is between 1 percent and 3.95 percent. In another embodiment, the amount of lidocaine is about 1 percent. In yet another embodiment, the amount of lidocaine is about 2 percent. In still another embodiment, the amount of lidocaine is about 3 percent. In a further embodiment, the amount of lidocaine is 3.95 percent.

In yet another embodiment, the patches of the present invention can further include one or more additional compatible active ingredients which are aimed at providing the composition with another pharmaceutical effect in addition to that provided by lidocaine. "Compatible" as used herein means that the components of such a composition are capable of being combined with each other in a manner such that there is no interaction that would substantially reduce the efficacy of the composition under ordinary use conditions.

Such additional active ingredients include, but are not limited to penetration enhancers, and agents that reduce skin discomfort such as anti-inflammatory agents. In one embodiment, a combination of local anesthetics, such as are known in the art, can be comprised in a single patch.

In one embodiment, the patch of the present invention is infused with penetration enhancers or permeation enhancing agent which aid in treatment effectiveness by facilitating delivery of the lidocaine. The term "penetration enhancer" as used herein refers to an agent known to accelerate the delivery of a substance through the skin. Suitable penetration enhancers usable in the present invention include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark AzoneR™ from Whitby Research Incorporated, Richmond, Va.), alcohols including menthol, and the like. In one embodiment, the permeation enhancement agent is menthol.

The permeation enhancer may also be a vegetable oil. Such oils include, for example, safflower oil, cottonseed oil and corn oil. Additional penetration enhancers may generally be found in Remington's Pharmaceutical Sciences, $18^{th}$ or $19^{th}$ editions, published by the Mack Publishing Company of Easton, Pa. which is incorporated in full herein by reference.

In one embodiment, the patch of this invention further comprises a permeation enhancement agent in an amount effective to enhance treatment. In certain embodiments, the permeation enhancement agent is a component of the composition. In alternate embodiments, the permeation enhancement agent is an active ingredient. In some embodiments, the composition of this invention comprises a permeation enhancement agent. In another embodiment, the permeation enhancement agent is menthol.

As used herein, the term "enhance treatment" refers to an amount of a permeation agent needed to enhance the permeation of an active ingredient, to enhance the reduction of pain experienced by a subject or to reduce side effects including skin discomfort resulting from administration of a patch of this invention, or any combination thereof. The term "enhance treatment" may herein also be referred to as "increase effective treatment" Enhanced treatment may result in an increase of an active ingredient permeating the skin. Alternatively, enhancement may result in a more rapid rate of an active ingredient permeating the skin then would occur without such treatment.

In one embodiment, a treatment-enhancing amount of a permeation enhancing agent can be about 1 percent to about 5 percent. In another embodiment, a treatment-enhancing amount of a permeation enhancing agent can be about 1 percent to about 16 percent. In yet another embodiment, a treatment-enhancing amount of a permeation enhancing agent can be about 3-5 percent, wherein these percentages are expressed as weight per weight of the composition comprised in the patch. In another embodiment, the permeation enhancement agent is menthol.

As used herein, reference of a percent amount of an active ingredient "by weight", herein refers to the percent expressed as weight per weight of the composition comprised in the patch.

The patch of the present invention also can be infused with an anti-inflammatory agent to reduce skin discomfort. As used herein "inflammation" refers to a response to infection and injury in which cells involved in detoxification and repair are mobilized to the compromised site by inflammatory mediators. Thus, the body's response may include edema, vasodilation, fever and pain. The term "skin discomfort" is used herein to refer to burning, stinging, itching, tingling, loss of feeling or heightened sensitivity of the skin. "Steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof. In one embodiment, a patch of this invention includes at least one anti-inflammatory agent. In another embodiment, a patch of this invention does not include an anti-inflammatory agent.

Preferably, the additional active ingredients are added in a treatment-enhancing amount. As used herein a "treatment-enhancing amount" refers to an amount that is effective to accomplish the desired effect. Typically, such an effective amount is an amount between about 0.1 up to about 10 percent as weight per weight of the composition. More typically a treatment-enhancing amount would be between about 1 to about 5 percent. In one embodiment, the patch and methods of this invention comprise lidocaine and additional active ingredients in a treatment-enhancing amount.

Preferably, a treatment-enhancing amount of anti-inflammatory agent used to reduce skin discomfort is about 1 percent to about 5 percent, preferably about 1 percent to about 3 percent, and most preferably about 1 percent, wherein these percentages are expressed as weight per weight of the composition.

In other embodiment, the patch of the present invention can be used in conjunction with rehabilitation modalities, such as ultrasound, magnetophoresis, iontophoresis or a battery powered electronic stimulant. As used herein, the term "magnetophoresis" refers to the motion of dispersed magnetic particles relative to a fluid under the influence of a magnetic field. Magnetophoresis may provide enhancing drug delivery across biological barriers, including intact skin, as illustrated in FIG. 2. Introduction of a drug or additional active ingredient through intact skin by the application of a direct electric current in iontophoresis may provide enhanced drug delivery when used in combination with a patch of this invention. In other embodiments, other patches described herein may be used in combination with iontophoresis. In one embodiment, iontophoresis acts as a transdermal delivery system in which a substance bearing a charge is propelled through the skin by a low electrical current. This method can be used to drive a drug across the skin barrier, as is done with pilocarpine to stimulate sweating in the sweat chloride test for cystic fibrosis. Iontophoresis can also be used in the reverse direction to draw a molecule such as glucose through the skin.

Methods utilizing electromotive enhancement treatments such as iontophoresis or magnetophoresis can provide faster relief to a subject, can increased an amount of an active ingredient penetrating into the skin or deeper tissue, can lead to an active ingredient penetrating deeper than the skin layers (epidermis, dermis), can provide longer relief from pain, can provide extended relief from pain or can provide stronger relief from pain, or any combination thereof. For example, in one embodiment, dependent on the strength of the charge used a drug may enter into skin and additionally into blood vessel found deeper under the skin.

In an additional embodiment, the patch of the present invention can be used in conjunction with rehabilitation therapies, such as heat, massage, manipulation, strength and stretching exercises, to maximize healing results with the elimination of muscle pain and spasm.

III. Patch Administration for Pain Reduction

Patches of the present invention have been described above. The patches can be administered at or adjacent to a site of pain to provide relief. In one embodiment, the pain is neuropathic pain, wherein administration of a patch of this invention reduces the neuropathic pain felt by a subject. In another embodiment, the pain is osteoarthritis pain, wherein administration of a patch of this invention reduces the osteoarthritic pain felt by a subject. In yet another embodiment, the pain is back pain, wherein administration of a patch of this invention reduces the back pain felt by a subject. In still another embodiment, the pain is a result of bone degeneration, wherein administration of a patch of this invention reduces the bone degeneration pain felt by a subject. In a further embodiment, the pain is associated with fibromyalgia, wherein administration of a patch of this invention reduces the pain associated with fibromyalgia felt by a subject. In another embodiment, the pain is associated with muscle strain, wherein administration of a patch of this invention reduces the muscle strain pain felt by a subject. In yet another embodiment, the pain is associated with muscle sprain, wherein administration of a patch of this invention reduces the muscle sprain pain felt by a subject. In still another embodiment, the pain is that associated with carpal tunnel syndrome pain, wherein administration of a patch of this invention reduces the carpal tunnel syndrome pain felt by a subject. In a further embodiment, the pain is that associated with any combination of diseases or disorders able to be relieved by local and/or deep tissue pain relief, wherein administration of a patch of this invention reduces the pain felt by a subject.

In one embodiment, a method for reducing pain in a subject comprises applying on a skin surface of the subject, at or near the site of pain, a patch comprising a lidocaine composition, wherein the application provides for transdermal delivery of an amount of lidocaine sufficient to reduce neuropathic pain in the subject. The methods of this invention may reduce pain resulting from different diseases, disorders or condition including neuropathic pain, osteoarthritis pain, back pain, degenerative bone pain, pain associated with carpal tunnel syndrome, pain associated with fibromyalgia, pain associated with muscle strain or pain associated with muscle sprain or any combination thereof.

As used herein, the term "administration" refers to applying, e.g., adhering a patch comprising a lidocaine formulation on a skin surface of a subject.

In one embodiment, administration of a patch provides immediate or nearly immediate relief, e.g., reduction of pain. In another embodiment, administration of a patch provides long term relief, e.g., reduction of pain. In yet another embodiment, administration of a patch provides both immediate or nearly immediate and long-term relief, e.g., reduction of pain.

The patches described herein can be administered at or adjacent to the sites of pain to provide relief. The patches can be administered once a day, for example, for fast, long term pain relief, e.g., pain relief is starts relatively quickly and is maintained over an extended period of time. As used herein the terms "reduction of pain" and "pain relief" are interchangeable with all the same meanings. In one embodiment, application of a patch may reduce the pain suffered by a subject completely or almost completely. In another embodiment, application of a patch may reduce the pain suffered by a subject by about 50 to almost 100 percent. In yet another embodiment, application of a patch may reduce the pain suffered by a subject by about 50 to 90 percent. In still another embodiment, application of a patch may reduce the pain suffered by a subject by about 80 to 90 percent. In a further embodiment, application of a patch may reduce the pain suffered by a subject by about 70 to 80 percent. In one embodiment, application of a patch may reduce the pain suffered by a subject by about 50 to 70 percent. In still another embodiment, application of a patch may reduce the pain suffered by a subject by less than 50 percent.

In one embodiment a patch of this invention is applied for between about 8 to 12 hours. In one embodiment a patch is applied for about 8 hours. In another embodiment a patch is applied for about 9 hours. In yet another embodiment, a patch is applied for about 10 hours. In still another embodiment, a patch is applied for about 11 hours. In a further embodiment, a patch is applied for about 12 hours.

A patch of the present invention is applied on the skin surface at a site or adjacent to a painful region. In some embodiments, multiple patches may be applied at the same time. Patches may be applied in the same region, an adjacent region or regions distal from one another. Fresh patches may be reapplied after a 24 hour period counted from the time the previous patch was administered.

In some embodiments, the patch is applied to the painful skin and subcutaneous structures in order to effect pain relief while avoiding the side effects associated with systemic delivery. Pain relief is obtained within minutes to hours and lasts for periods of approximately three to six hours to 24 hours. The patches are applied such that the dosage is sufficient to provide an effective dose in the painful area or immediately adjacent areas, to ameliorate or eliminate pain and other unpleasant sensations such as itching. In one embodiment, pain is reduced for at least 12 hours. In another embodiment, pain is reduced for at least 24 hours. In yet another embodiment, pain is reduced for more than 24 hours.

The appropriate dosages for pain treatment by way of patches of the present invention are determined by a variety of factors. The rate at which the active components are absorbed is a function of skin permeability. Skin permeability varies between different sites on a patient's body and depends on the thickness of the stratum corneum. The stratum corneum is the outer-most layer of skin and is the main source of penetration and permeation resistance for dermally administered drugs. For example, the permeability, in general, increases in order from planter foot arch, lateral ankle, palm, ventral forearm, dorsal forearm, back, chest, thigh, abdomen, scalp, axilla, forehead, and scrotum; see R. C. Wester. & H. I. Maibach, Regional variation in Percutaneous Absorption, in Percutaneous Absorption, Mechanism, Methodology, Drug Delivery 111-119 (R. L. Bronaugh & H. I. Maibach eds., 2nd ed. 1989), hereby expressly incorporated in full herein by reference.

The delivery rate of an active ingredient from a patch, e.g., lidocaine, of the present invention that is required for proper pain relief is determined by a variety of factors. One important factor regarding delivery rate is the surface areas of the active ingredients in contact with a patient's skin. In general, the larger the contact surface area, the higher the rate of delivery. Different delivery rates of an active ingredient may be needed depending on the severity of pain felt. The surface areas of components can adjusted to provide the desired delivery rate of an active ingredient to a patient.

In addition, delivery rate may be enhanced as describe above using chemical enhancement agents, for example menthol and/or physical enhancement methodologies, for example iontophoresis, a battery powered electronic stimulant or magnetophoresis. In one embodiment, methods of this invention for reducing neuropathic pain include treatment enhancing amounts of a permeation agent. In one embodiment, methods of this invention for reducing neuropathic pain include treatment enhancing methodologies including iontophoresis, a battery powered electronic stimulant or magnetophoresis.

Methods of this invention include transdermal administration of active ingredients, e.g., lidocaine.

In one embodiment, methods of this invention for reducing pain in a subject comprise applying on a skin surface of the subject, at or near the site of pain a patch comprising compositions comprising lidocaine at less then 4 percent by weight. In another embodiment, methods of this invention use lidocaine at between 1 and 3.95 percent by weight. In yet another embodiment, methods of this invention use lidocaine at 1 percent by weight. In still another embodiment, methods of this invention use lidocaine at 2 percent by weight. In a further embodiment, methods of this invention use lidocaine at 3 percent by weight. In one embodiment, methods of this invention use lidocaine at 3.95 percent by weight.

In one embodiment the composition of this invention comprises local anesthetic and drugs not traditionally associated with local anesthetic properties but which have a local anesthetic effect. Non limiting examples of such drugs include for example, non-narcotic analgesics, such as, acetylsalicylic acid, ketoprofen, piroxicam, diclofenac, indomethacin, ketorolac, rofecoxib, and celecoxib, and pharmaceutically acceptable salts thereof, or mixtures thereof.

As used herein the term "drug" refers to a substance used in the diagnosis, treatment, or prevention of a disease or medical condition or an active component of a medication. Of course, the term "drug" encompasses local anesthetics and/or analgesics. In one embodiment, a drug of this invention is lidocaine.

Reference is made to FIG. 1 at 100. A first step in any treatment method of this invention may be selection of an appropriate patch for reduction of the pain suffered by a subject. Patches may be cut to the size and shape need to administer an appropriate dose and/or cover a particular surface of skin (See FIG. 1, step 102). For instance, an appropriate patch may be perforated to provide flexibility.

Following this, a patch may be applied to the skin surface for an effective time period (See FIG. 1, step 104). For effective use, a patch should be in contact with a surface of the skin and remain in place for the duration of the treatment. In order that a patch remains in place, an adhesive may be comprised as part of a patch. Alternatively, an adhesive, such as an adhesive strip or tape may be used to hold the patch in place. For example, a patch may be adhered to a patient's back through the use of a drug-in-adhesive patch. In an alternative example, a patch may both included an adhesive and be perforated to allow the patch to stretch, wherein a patch may be wrapped fully or partially around a subject's body appendage, e.g., a leg, arm, finger or neck.

The selected patch may comprise a composition comprising permeation enhancers. Alternatively, physical methodologies such as iontophoresis, a battery powered electronic stimulant or magnetophoresis may be employed to enhance the permeation of at least one active ingredient. Examples of drug delivery by iontophoresis are shown in FIG. 2. Technique using a small electric charge to deliver active ingredient through the skin, e.g., iontophoresis, may enhance permeation of at least one active ingredient. Iontophoresis may be imagined to be an injection without the needle. The process is a non-invasive method of propelling high concentrations of a charged substance, e.g., lidocaine, transdermally by repulsive electromotive force using a small electrical charge applied to an iontophoretic chamber containing a similarly charged active agent and its vehicle."

Following the recommended time period of application, the patch may be removed from the skin surface (See FIG. 1, step 106). Relief from pain may continue even though the patch has been removed. Following a period of 24 from the initial administration, this cycle of use may employed by a subject. This may be significant for sufferers of chronic pain.

In one embodiment, the term "a" or "one" or "an" refers to at least one. As used in the specification and claims, the forms "a," "an" and "the" include singular as well as plural references unless the context clearly dictates otherwise.

In one embodiment the phrase "two or more" may be of any denomination, which will suit a particular purpose. In one embodiment, "about" may comprise a deviance from the indicated term of +1%, or in some embodiments, −1%, or in some embodiments, ±2.5%, or in some embodiments, ±5%, or in some embodiments, ±7.5%, or in some embodiments, ±10%, or in some embodiments, ±15%, or in some embodiments, ±20%, or in some embodiments, ±25%.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for reducing pain from degenerative bone disease in a subject comprising applying on a skin surface of the subject a patch for transdermal delivery of lidocaine consisting of a low dose of a therapeutically effective amount of lidocaine and an adhesive that acts as a pharmaceutically acceptable carrier, a permeation enhancer and an excipient wherein said active ingredient consists of 3.6 percent to less than 5 percent lidocaine by weight and wherein said pain from degenerative bone disease consists of pain from microarchitectural deterioration of bone tissue.

2. A method for reducing pain from degenerative bone disease in a subject comprising applying on a skin surface of the subject a patch for transdermal delivery of lidocaine consisting of a low dose of a therapeutically effective amount of an active ingredient and an adhesive that acts as a pharmaceutically acceptable carrier, a permeation enhancer and an excipient wherein said active ingredient consists of 3 to less than 4 percent lidocaine by weight and wherein said pain from degenerative bone disease consists of pain from low bone mass.

3. The method of claim 1 wherein said permeation enhancer comprises menthol.

4. The method of claim 2 wherein said permeation enhancer comprises menthol.

5. A method for reducing pain from low bone mass in a subject without an injection comprising, applying on a skin surface of a subject a patch for transdermal delivery of lidocaine consisting of a low dose of a therapeutically effective amount of an active ingredient and an adhesive that acts as a pharmaceutically acceptable carrier, and a permeation enhancer, and an excipient; wherein pain from low bone mass consists of chronic back pain and wherein said low dose of the therapeutically effective amount of said active ingredient consists of less than 5 percent lidocaine by weight.

6. The method of claim 5 wherein said permeation enhancer comprises menthol.

* * * * *